(12) United States Patent
Mrva et al.

(10) Patent No.: US 7,797,058 B2
(45) Date of Patent: Sep. 14, 2010

(54) DEVICES, SYSTEMS, AND METHODS EMPLOYING A MOLDED NERVE CUFF ELECTRODE

(75) Inventors: Joseph J. Mrva, Willoughby Hills, OH (US); James Coburn, Cleveland Heights, OH (US); Robert B. Strother, Willoughby Hills, OH (US); Geoffrey B. Thrope, Shaker Heights, OH (US)

(73) Assignee: NDI Medical, LLC, Cleveland, OH (US)

( * ) Notice: Subject to any disclaimer, the term of this patent is extended or adjusted under 35 U.S.C. 154(b) by 144 days.

(21) Appl. No.: 11/196,995

(22) Filed: Aug. 4, 2005

(65) Prior Publication Data

US 2006/0030919 A1    Feb. 9, 2006

Related U.S. Application Data

(60) Provisional application No. 60/598,695, filed on Aug. 4, 2004.

(51) Int. Cl.
*A61N 1/05*    (2006.01)
(52) U.S. Cl. ...................................... 607/118; 606/129
(58) Field of Classification Search ................. 607/118; 606/129
See application file for complete search history.

(56) References Cited

U.S. PATENT DOCUMENTS

| | | | |
|---|---|---|---|
| 3,421,511 A | 1/1969 | Schwartz et al. | |
| 3,654,933 A | 4/1972 | Hagfors | |
| 3,774,618 A | 11/1973 | Avery | |
| 4,573,481 A | 3/1986 | Bullara | |
| 4,590,946 A | 5/1986 | Loeb | |
| 4,602,624 A * | 7/1986 | Naples et al. | 607/118 |
| 4,628,942 A * | 12/1986 | Sweeney et al. | 607/118 |
| 4,649,936 A | 3/1987 | Ungar et al. | |
| 4,750,499 A | 6/1988 | Hoffer | |
| 4,920,979 A | 5/1990 | Bullara | |
| 4,926,875 A | 5/1990 | Rabinovitz et al. | |
| 4,934,368 A | 6/1990 | Lynch | |
| 4,940,065 A | 7/1990 | Tanagho et al. | |
| 5,095,905 A | 3/1992 | Klepinski | |
| 5,265,608 A | 11/1993 | Lee et al. | |
| 5,289,821 A | 3/1994 | Swartz | |
| 5,324,322 A | 6/1994 | Grill, Jr. et al. | |
| 5,400,784 A | 3/1995 | Durand et al. | |
| 5,487,756 A | 1/1996 | Kallesoe et al. | |

(Continued)

OTHER PUBLICATIONS

Nerve Cuff Electrode With Shape Memory Alloy Armature: Design and Fabrication, Crampon et al., *Bio-Medical Materials and Engineering* 12 (2002) 397-410.

(Continued)

*Primary Examiner*—Scott M Getzow
*Assistant Examiner*—Joseph M Dietrich
(74) *Attorney, Agent, or Firm*—Ryan Kromholz & Manion, S.C.

(57) ABSTRACT

Devices, systems, and methods for recording, and/or stimulation, and/or blocking of a nerve make use of a molded cuff electrode. An electrically conductive surface is coupled to an inside surface of the cuff's elastic body. The electrically conductive surface and the body assume a coiled configuration in its natural state. An applicator tool having a body and a slider are used to implant the cuff electrode about a nerve.

16 Claims, 6 Drawing Sheets

U.S. PATENT DOCUMENTS

| | | | |
|---|---|---|---|
| 5,505,201 | A | 4/1996 | Grill, Jr. et al. |
| 5,531,778 | A | 7/1996 | Maschino et al. |
| 5,634,462 | A * | 6/1997 | Tyler et al. .................. 607/118 |
| 5,741,319 | A | 4/1998 | Woloszko et al. |
| 5,824,027 | A | 10/1998 | Hoffer et al. |
| 5,899,933 | A | 5/1999 | Bhadra et al. |
| 5,919,220 | A | 7/1999 | Stieglitz et al. |
| 5,938,596 | A | 8/1999 | Woloszko et al. |
| 6,292,703 | B1 | 9/2001 | Meier et al. |
| 6,308,105 | B1 | 10/2001 | Duysens et al. |
| 6,456,866 | B1 | 9/2002 | Tyler et al. |
| 6,600,956 | B2 * | 7/2003 | Maschino et al. ........... 607/118 |
| 6,907,295 | B2 | 6/2005 | Gross et al. |
| 2002/0055779 | A1 * | 5/2002 | Andrews .................... 607/118 |

OTHER PUBLICATIONS

"New Easy to Install Nerve Cuff Electrode Using Shape Memory Alloy Armature", Crampon et al., *Artificial Organs,* 23(5):392-395, 1999.

"Neural Morphological Effects of Long-Term Implantation of the Self-Sizing Spiral Cuff Nerve Electrode", Romero et al., *Medical & Biological Engineering & Computing,* 2001, vol. 39, pp. 90-100.

"Cuff Electrodes for Chronic Stimulation and Recording of Peripheral Nerve Activity", Loeb et al., *Journal of Neuroscience Methods,* 64 (1996), 95-103.

"Chronic Response of the Rat Sciatic Nerve Electrode", Tyler et al., *Annals of Biomedical Engineering,* vol. 31, pp. 633-642, 2003.

"A Spiral Nerve Cuff Electrode for Peripheral Nerve Stimulation", Naples et al., *IEEE Transactions on Biomedical Engineering,* vol. 35, No. II, Nov. 1988.

"Spiral Nerve Cuff Electrode for Recordings of Respiratory Output", Sahin et al., *The spiral Nerve Cuff Electrode,* 1997 American Physiologi-cal Societ, pp. 317-322.

"A Nerve Cuff Technique for Selective Excitation of Peripheral Nerve Trunk Regions", Sweeney et al., *IEEE Transactions on Biomedical Engineering,* vol. 37 No. 7, Jul. 1990.

\* cited by examiner

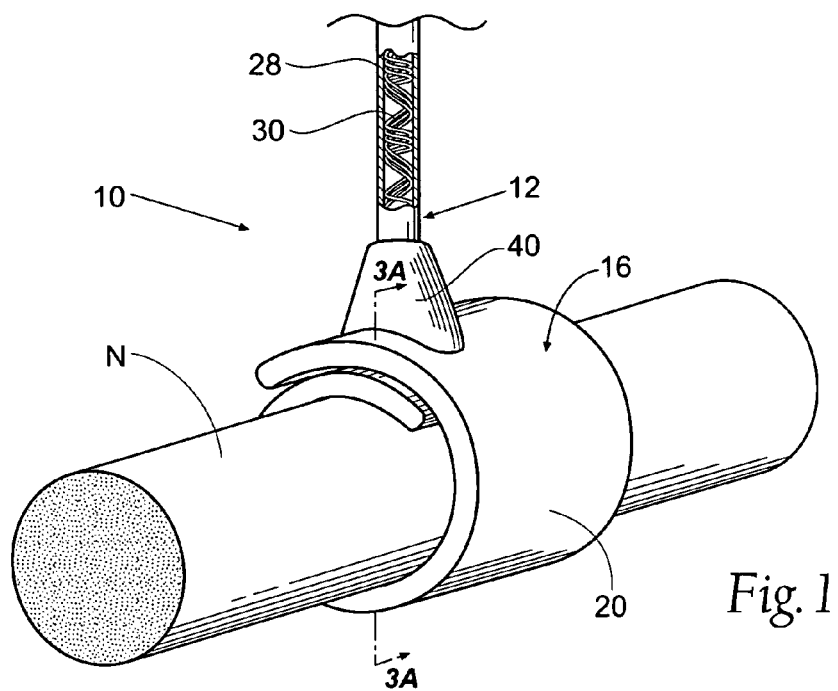
*Fig. 1*
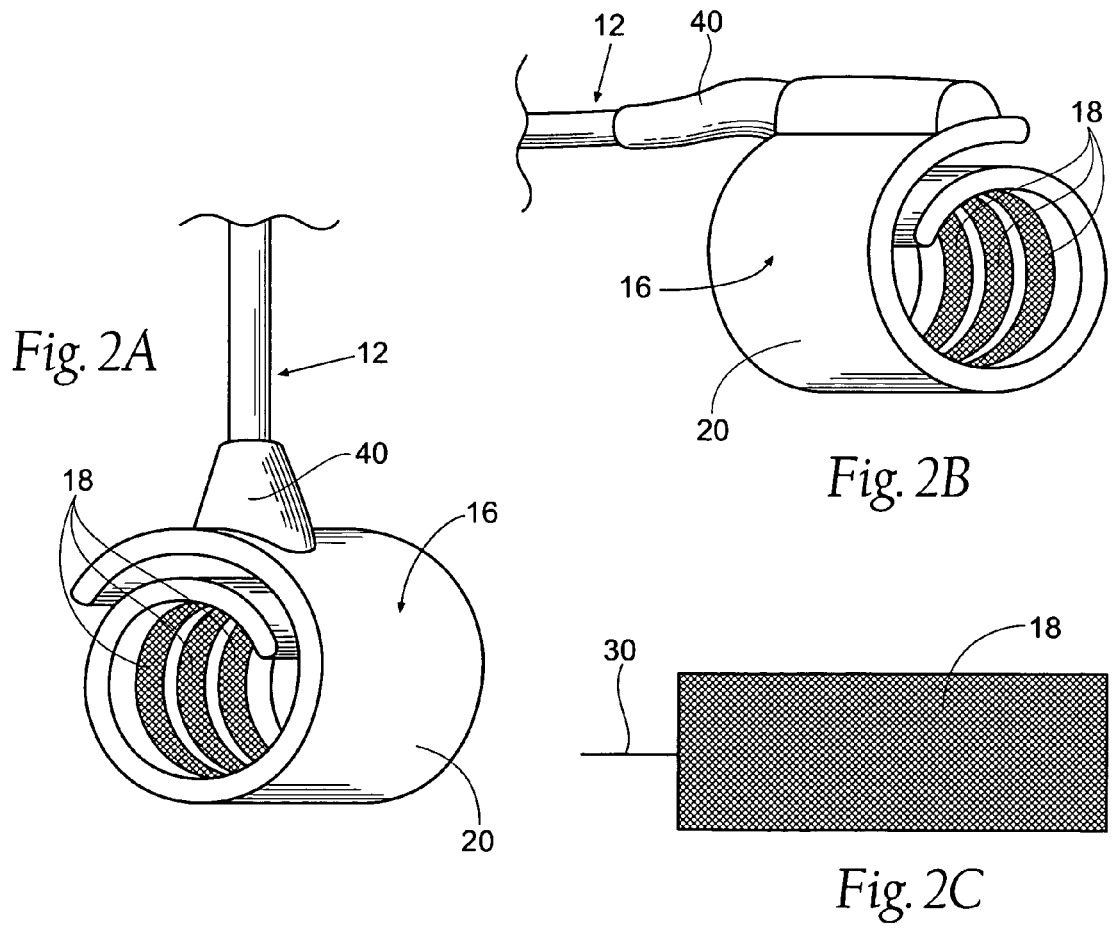
*Fig. 2A*
*Fig. 2B*
*Fig. 2C*

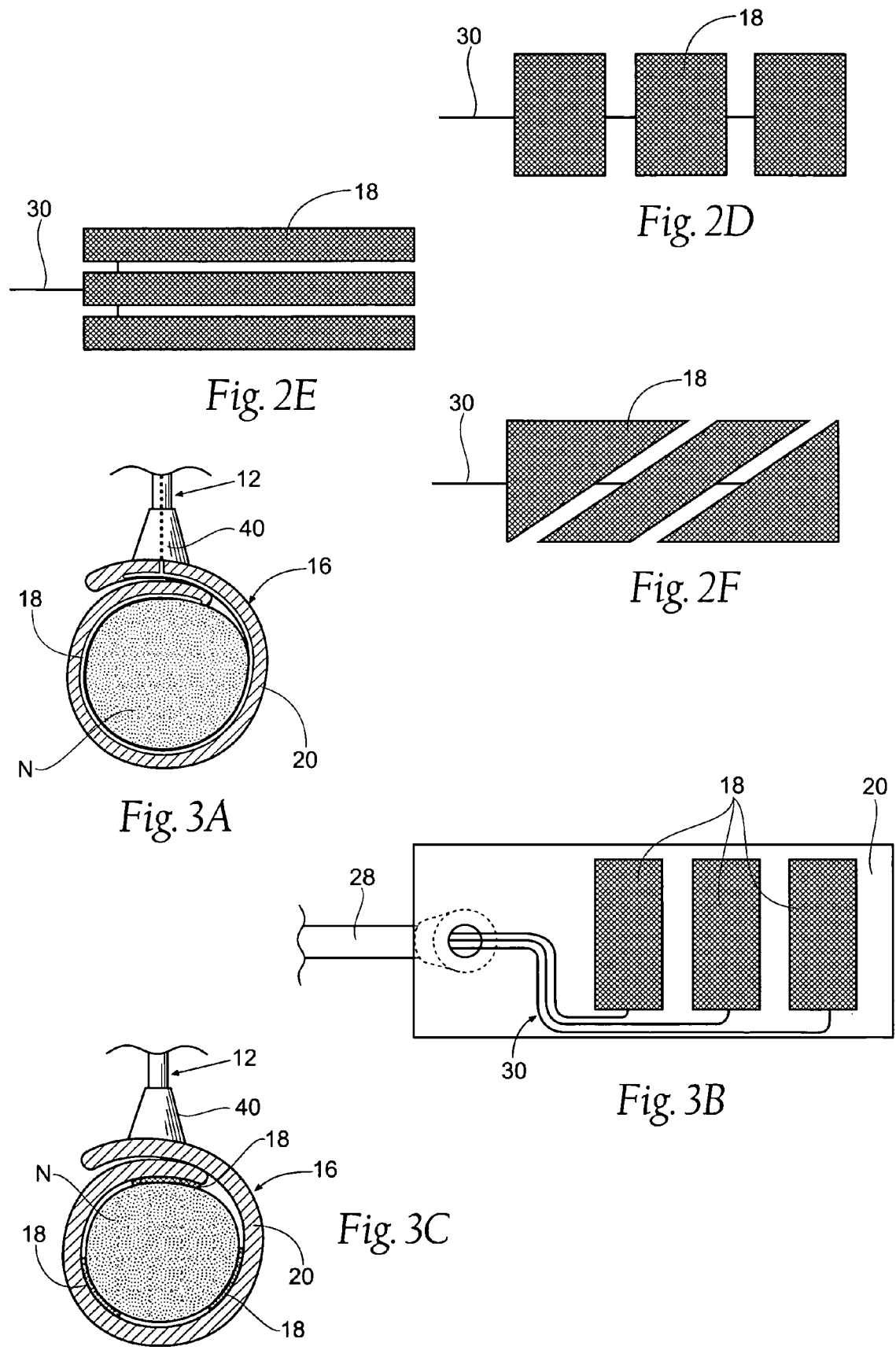

DEVICES, SYSTEMS, AND METHODS EMPLOYING A MOLDED NERVE CUFF ELECTRODE

RELATED APPLICATION

This application claims the benefit of U.S. Provisional Patent Application Ser. No. 60/598,695, filed Aug. 4, 2004, and entitled "Devices, Systems, and Methods Employing a Molded Nerve Cuff Electrode" which is incorporated herein by reference.

STATEMENT REGARDING FEDERALLY SPONSORED RESEARCH

This invention was made with government support under grant no. 1RNS051862-01 awarded by the National Institutes of Health, through the National Institute of Neurological Disorders and Stroke. The Government may have certain rights in the invention.

FIELD OF THE INVENTION

This invention relates to nerve cuff electrodes for neuronal recording, stimulation, and blocking in animals, including humans.

BACKGROUND OF THE INVENTION

In the last forty years, neuromodulation and neurostimulation implantable technologies have been used extensively for a variety of indications. As such, the components of these systems have developed a significant track record and their actions on the body are reasonably well understood. Many of these systems use implantable pulse generators (IPG's) and electrodes to deliver charge to the site of a biological tissue, i.e., a nerve. By using an appropriate low frequency waveform, the system induces action potentials in a targeted nerve (or nerves) that create the desired effect. It should be noted that the ability to create action potentials does not necessarily require direct contact with the nerve.

However, certain applications may require a direct contact with the nerve. One example is selective stimulation or recording from a portion of a nerve bundle. Another example is the blocking of conduction of action potentials using high frequency signals.

High frequency nerve blocks are immediately reversible, which makes them a more attractive clinical solution for conditions that have traditionally required treatments that are not reversible and permanent, such as nerve transections. Unlike other indications that attempt to selectively recruit nerve fascicles, where current is steered to target portions of the nerve, the conduction nerve block requires a saturation of the nerve with a current field. This saturation effect is best achieved with a circumferential set of electrode bands in a tri-polar configuration surrounding the entire nerve or other multi-pole configurations with the outermost bands at the same potential.

Kilgore and Bhadra have investigated the use of a low voltage, high frequency signal to create a block [Kilgore et al., 2004]. Their research has to date shown that a 5 kHz to 30 kHz balanced biphasic waveform produced a complete motor block in 34 of 34 nerves tested in nerves of various small and large mammals, including dogs. The block was completely reversible in all cases.

Similar results have been achieved in mammals for acute applications but with more variability in results. It has been demonstrated that a major factor in the efficacy and repeatability of the block is the circumferential contact that the electrode has to the targeted nerve. The results described above have been obtained using the spiral cuff electrode, first patented in 1986 by Naples, Mortimer, et al (U.S. Pat. No. 4,602,624). It is a laminated assembly of two Silastic sheets (Dow Corning), with one layer stretched during the glue-up process (Silastic Adhesive). Once the assembly is freed from the press, it naturally curls towards the stretched side. The flat edge is typically long enough so that the cuff makes at least one and half revolutions of the nerve. This seals the cuff to provide an insulation barrier so that current does not leak around the cuff. The two laminates carry platinum electrodes, with windows cut out on the stretched side so that current can be conducted inwards.

Existing spiral cuff electrode do not reliability interface to small nerves. The stiffness of the platinum prevents the electrode from fully conforming to the small diameter of the nerve. The stiffness also does not allow the electrode to be fully adaptive, accommodating post-operative swelling of the nerve, which commonly occurs. Furthermore, the manufacturing process described in the Naples et al. Patent to produce the electrode is hand-labor intensive with low repeatability of key process parameters.

SUMMARY OF THE INVENTION

The invention provides devices, systems, and methods for which employ a molded nerve cuff electrode.

One aspect of the invention provides an implantable cuff electrode for placement about a biological tissue. The implantable cuff electrode comprises an elastic body having an elastic memory, at least one electrically conductive surface coupled to an inside surface of the elastic body, and the body and electrically conductive surface assume a coiled configuration in its natural shape, the coiled configuration allowing an intimate contact between the electrically conductive surface on the inside surface of the elastic body and the biological tissue surrounded.

Another aspect of the invention provides an applicator tool for implanting a cuff electrode about a biological tissue, the applicator tool comprising an applicator body having a handle, the applicator body comprising an open ended inverted trough for fitment over a portion of a biological tissue, the applicator body including a slider carried on the applicator body and moveable along the axis of the applicator body between a forward position and an aft position, and a linkage mechanism coupled to the handle and the slider to affect movement of the slider fore and aft.

An additional aspect of the invention provides a method of manufacturing a cuff electrode, the method comprising conductively coupling at least one wire to at least one electrically conductive surface, positioning the at least one electrically conductive surface in a spiral configuration within a mold, pouring or injecting an elastomer material into the mold, allowing the mold to cure, and removing the cuff electrode from the mold.

Yet another aspect of the invention provides a system for neuronal recording and/or stimulating and/or blocking, the system comprising an implantable lead having a proximal end and a distal end, a cuff electrode coupled to the distal end, the cuff electrode comprising an elastic body having an elastic memory, at least one electrically conductive surface coupled to an inside surface of the elastic body, and the body and electrically conductive surface assuming a coiled configuration in its natural shape, the coiled configuration allowing an intimate contact between the electrically conductive surface on the inside surface of the elastic body and the biological tissue surrounded, wherein the lead encapsulates a wire element, and wherein the proximal end of the lead is coupled to a stimulation pulse generator.

And yet another aspect of the invention provides a method of installing a cuff electrode about a biological tissue, the method comprising uncoiling the cuff electrode, positioning the cuff electrode on an applicator tool, the applicator tool comprising an applicator body having an open ended inverted trough for fitment over a portion of the biological tissue, the applicator body including a slider carried on the applicator body and moveable along the axis of the applicator body between a forward position and an aft position, and a linkage mechanism coupled to the handle and the slider to affect movement of the slider fore and aft, the cuff electrode being positioned on the applicator body forward of the slider, placing the applicator tool in a targeted position on the biological tissue, moving the linkage mechanism to move the slider forward and eject the cuff electrode from the applicator body onto the biological tissue, and removing the applicator tool.

Other features and advantages of the inventions are set forth in the following specification and attached drawings.

BRIEF DESCRIPTION OF THE DRAWINGS

FIG. 1 is a perspective, diagrammatic view of a molded cuff electrode implanted about a nerve.

FIG. 2A is a perspective view of the molded cuff electrode shown in FIG. 1 prior to implantation.

FIG. 2B is a perspective view of an alternative embodiment of the molded cuff electrode shown in FIG. 1, showing the lead extending generally parallel from the cuff electrode.

FIGS. 2C through 2F are plan views showing both solid and segmented embodiments for the electrically conductive surface.

FIG. 3A is a side section view of the molded cuff electrode taken generally along line 3A-3A on FIG. 1.

FIG. 3B is a plan view of an alternative embodiment of the conductive surfaces configuration.

FIG. 3C is a side section view of the alternative embodiment shown in FIG. 3B positioned about a nerve N.

Figure 4A:
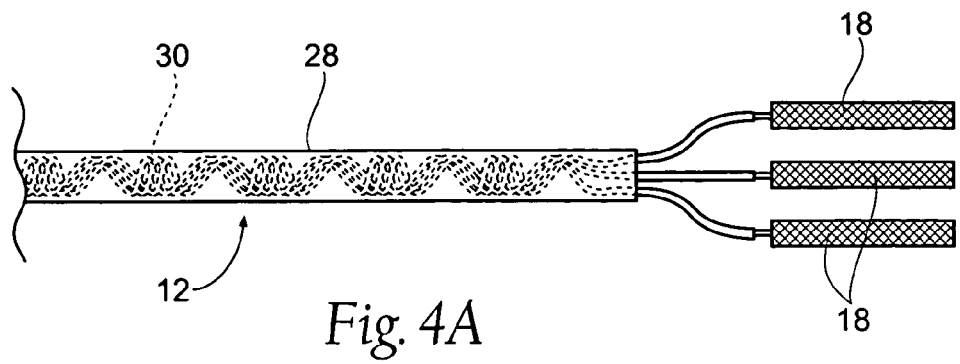
FIGS. 4A to 4E are diagrammatic views of a molding process by which the molded cuff electrode shown in FIG. 2A can be made.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. Molded Nerve Cuff

FIG. 1 shows an implant system 10 for recording, and/or stimulation, and/or blocking of a biological tissue, i.e., a nerve N in an animal, including a human. The system includes an implantable lead 12 having a proximal and a distal end. The distal end carries a cuff electrode 16.

As FIG. 2A shows, the cuff electrode 16 includes at least one electrically conductive surface 18. In the illustrated embodiment, there are three individually controllable electrically conductive surfaces 18, although more or less may be used. The surface 18 may be solid, as shown in FIG. 2C, or the surface may be segmented into isolated conductive segments electrically coupled by a wire. Alternative embodiments having segmented conductive surfaces 18 are shown in FIGS. 2D through 2F. It is to be appreciated that additional alternative configurations are possible as well.

In this arrangement, the lead 12 (see FIG. 1) comprises a molded component 28, which encapsulates a coiled trifilar stranded wire element 30. Each wire of the element 30 is coupled to one of the electrically conductive solid or segmented surfaces 18. These surfaces may be manufactured using a thin film of metal deposited on a liquid crystal polymer substrate, or from strips of platinum, for example.

As FIG. 2A shows, the cuff electrode 16 comprises a body 20 that may be molded from a low durometer elastomer material, e.g., silicone. The electrically conductive surfaces 18 are integrated with the body 20 during the molding process, as will be described in greater detail later.

The molded body 20 of the cuff electrode 16 is shaped or formed during the molding process to normally assume a curled or tubular spiral or rolled configuration. As shown in FIG. 2A, in its normal coiled condition, the body 20 extends in a spiral having a range of about 450 degrees to about 560 degrees from end to end, and in one embodiment about 540 degrees from end to end. The body 20 can be elastically uncoiled to increase its inner diameter (as FIGS. 1 and 3A show), e.g., to be initially fitted about the periphery of the nerve N, and in response to post-operative changes in the diameter of the nerve N that might occur due to swelling. The elasticity of the body 20 wraps the electrically conductive surfaces snugly against the periphery of the targeted nerve N. The elasticity of the body 20 is selected to snugly wrap about the nerve N without causing damage or trauma. To this end, it is believed desirable that the elastic memory of the cuff electrode 16 exhibits a predictable and repeatable pressure vs. diameter relationship that gradually increases pressure with increase in diameter to allow the electrode to fit snuggly about the periphery of a nerve, but not too tightly to cause damage (i.e., exerts a maximum pressure about the nerve N that does not exceed about 20 mmHg).

As FIG. 2A shows, the electrode 16, being a molded component, desirably includes a molded or over-molded section forming a strain relief boot 40 at the junction between the lead 12 and the cuff body 20. The boot 40 strengthens the junction, to resist the effect of torque forces that might be applied during implantation and use along the lead 12. In addition, the strain relief boot 40 helps to prevent tension and/or motion from damaging the lead to cuff interface for a longer flex life. FIG. 2B shows an alternative embodiment where the lead 12 and strain relief boot 40 are generally parallel to the cuff body 20. The strain relief boot 40 may take on any desired shape (i.e., coiled, bent, cone, or zigzag) to aid in its strain relief properties and to improve manufacturability. It is to be appreciated that the lead to cuff interface may be at any desired angle and is not limited to a parallel or perpendicular configuration.

As FIG. 3A shows, when wrapped about the nerve N, the electrically conductive surfaces 18 make and sustain circumferential contact substantially about the entire periphery of the nerve N. In an alternative embodiment shown in FIGS. 3B and 3C, the electrically conductive surfaces 18 may be positioned so as to make contact with the nerve N along the axis of the nerve, and around only a portion of the circumference of the nerve N. FIG. 3B shows an uncoiled cuff body 20 including three electrically conductive surfaces 18. FIG. 3C shows the conductive surfaces 18 positioned along a length (the axis) of the nerve N.

In a representative embodiment, the body 20 possesses a minimum diameter (when in its normally coiled condition) of as small as one mm, which makes it well suited for implantation about small nerves. The minimum diameter of the body 20 can, of course, be molded to possess larger minimum diameters, to provide a family of nerve cuff electrodes 16 of different diameters that accommodate the range of diameters of human and animal nerves, from small to large.

The electrically conductive surfaces 18 are made, e.g., from strips of platinum, either as one long strip, or as segmented strips that are connected to each other by at least one wire. In addition, these or alternative configurations may be manufactured using a thin film of metal deposited on a liquid crystal polymer substrate. The electrically conductive surface 18 measures at least one mm of length along the axis of the nerve N and at least one mm of width along the circumference of the nerve N. In one representative embodiment, the strips 18 each measure about 10 mm×2 mm×0.0254 mm in length, width, and thickness, respectively. The geometry allows the molded elastomeric body 20 to securely hold the strips without migration, with the surfaces 18 exposed for contact with the nerve. In the illustrated embodiment, the electrically conductive surfaces 18 are carried in an exposed array circumferentially against and along the axis of the nerve N. This geometry is well suited for applying nerve conduction blocks, but has application for use in other indications as well. Other geometries and configurations can, of course, be used for other indications.

II. Making the Molded Nerve Cuff

Figure 4B:
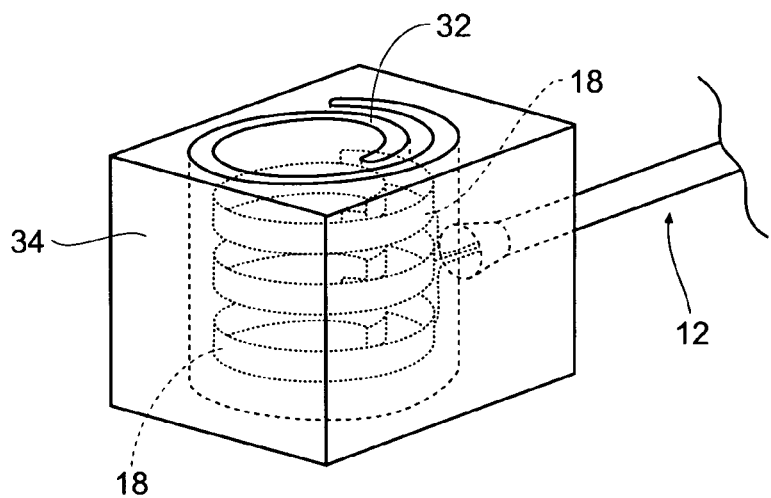
Figure 4C:
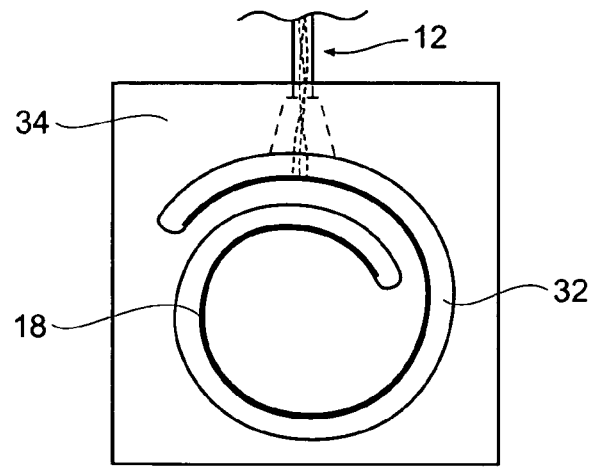
Figure 4D:
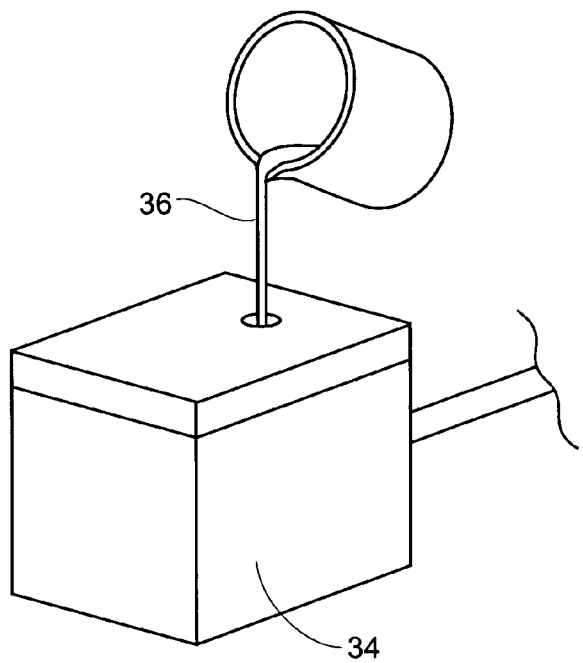
Figure 4E:
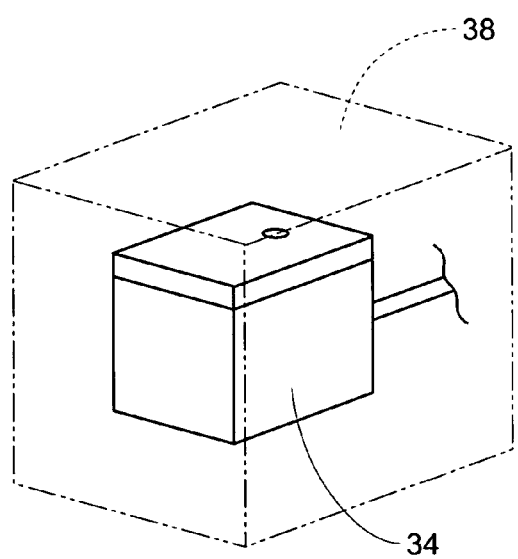

FIGS. 4A to 4E show a representative process for molding the cuff electrode 16. As FIG. 4A shows, the extruded material 28 at the end of the lead 12 is stripped away to expose the wires of the trifilar wire element 30. Each wire of the element 30 is welded or otherwise conductively coupled to one of the strip contact surfaces 18. As FIGS. 4B and 4C show, the strip contact surfaces 18 are then wrapped in a desired spiral configuration around the core 32 of a mold 34. The surfaces 18 can held in this spiral configuration within the core 32 using, e.g., a vacuum or implantable safe adhesive. As FIG. 4D shows, the mold 34 is closed, and an elastomer material 36, e.g., a two part, translucent, pourable silicone elastomer (e.g., Nusil MED-4211), is poured or injected into the mold 34. As FIG. 4E shows, the mold 34 is allowed to cure for a predetermined period of time exposed to a predetermined heat condition. For example, the mold may be cured at room temperature for an extended period of time or the mold may be cured at an elevated temperature for a reduced amount of time. In one embodiment, the mold 34 may be placed in a preheated oven 38 at 150 degrees Celsius for about one hour. The mold 34 is then removed from the oven 38, opened, and the body 20 removed from the mold 34. Taken from the mold, the resulting electrode 16 comprises the coiled configuration shown in FIG. 2A.

Because the electrode 16 is molded in a coiled configuration, the manufacturing process is reliable and repeatable, compared to a manufacturing process for conventional coiled nerve cuff electrodes, in which the electrode must be stretched into a coiled configuration. Molding typically also makes possible reasonable unit costs and can, by changing mold configurations, readily accommodate different geometries and configurations, to manufacture electrodes for different product requirements. Today, due to the advanced ability to model and cut molds using 3D modeling software, one can quickly retool for different product requirements, to accommodate diverse variations in the electrode design and placement.

III. Implanting the Molded Electrode Cuff

Due to its mechanical and physical properties, the molded cuff electrode 16 shown in FIG. 2A is, in use, well suited for placement about a peripheral nerve to deliver a reversible nerve conduction block. This is because the electrode 16 (i) reliably establishes and maintains circumferential contact about substantially the entire nerve periphery, (ii) exhibits a predictable and repeatable diameter vs. pressure curve, (iii) is adaptive to post-operative swelling, and (iv) resists the effects of translational and rotational forces to stay in place post-operatively.

Figure 5:
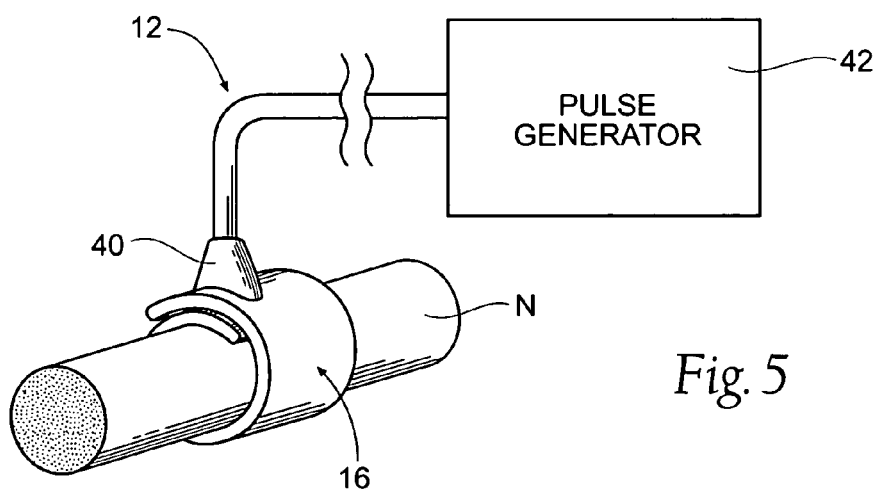
FIG. 5 is a perspective view of a molded cuff electrode as shown in FIG. 2A, coupled to a pulse generator to deliver a high frequency nerve conduction block to achieve a desired therapeutic result.

In this use (see FIG. 5), the proximal end of the lead 12 is coupled to a stimulation pulse generator 42. The pulse generator 42 includes a circuit that generates electrical waveforms that are capable of depolarizing the nerve across its entire cross section or selectively over just a portion of the nerve cross section, e.g., using high frequency waveforms (about 5 kHz to about 30 kHz).

A. Implant Applicator Tool

Figure 6A:
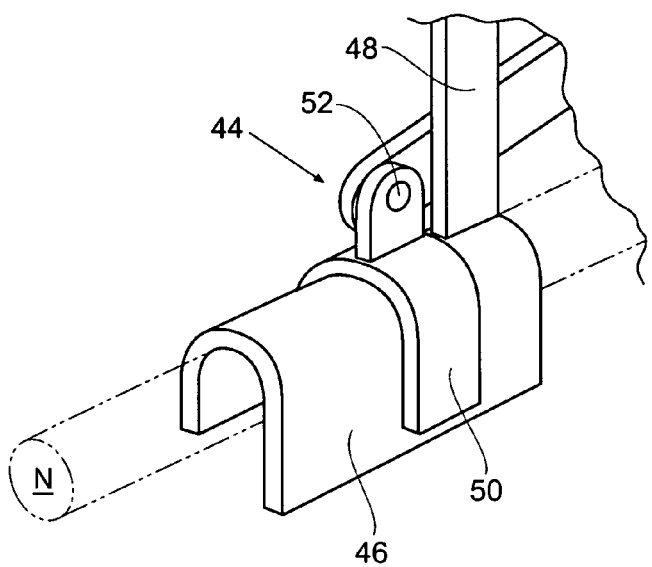
FIG. 6A is an applicator tool for placement of a molded cuff electrode of the type shown in FIG. 2A about a nerve, the applicator tool being shown before mounting of the electrode with the electrode delivery mechanism in a forward condition.
Figure 6B:
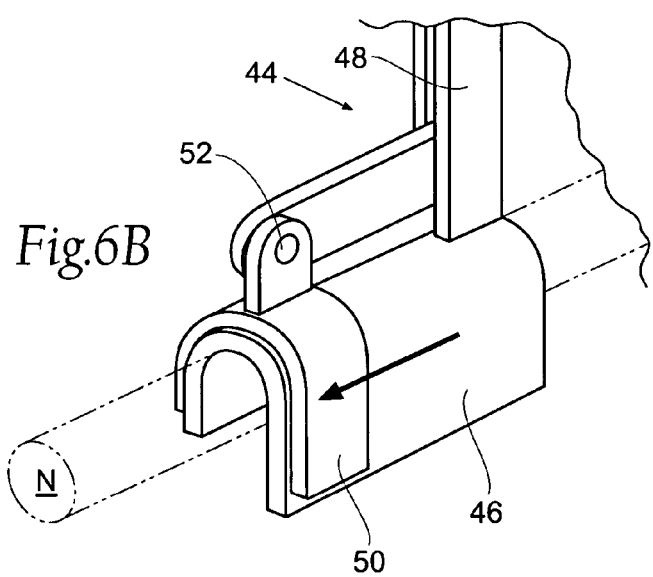
FIG. 6B is the applicator tool shown in FIG. 6A, the applicator tool being shown before mounting of the electrode with the electrode delivery mechanism in an aft condition.
Figure 6C:
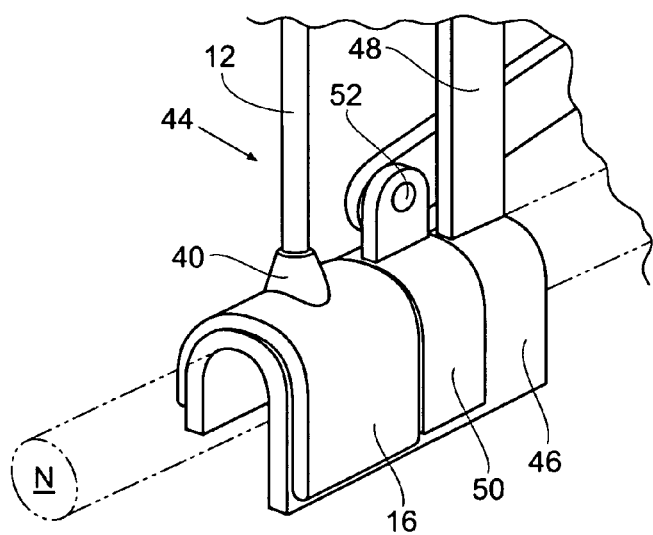
FIG. 6C is the applicator tool shown in FIG. 6A, the applicator tool being shown after mounting of the electrode with the electrode delivery mechanism in an aft condition.

As shown in FIGS. 6A to 6C, the implantation of the electrode 16 can be facilitated by use of an applicator tool 44. While tools of various configurations can be used, the applicator tool 44 shown in FIGS. 6A to 6C includes an applicator body 46 with a handle 48. As FIG. 6A shows, the applicator body 46 comprises an open ended, inverted trough for fitment over a portion of a nerve N. As will be described later, the curvilinear form of the body 46 accommodates mounting of the electrode 16 in an uncoiled condition.

The applicator tool 44 also includes a slider 50 carried on the body 46. The slider 50 moves along the axis of the body 46 between a forward position (FIG. 6B) and an aft position (FIG. 6A). A scissors-type linkage 52 is coupled to the handle 48 so an operator can easily affect movement of the slider 50 fore and aft. Opening the linkage 52 moves the slider 50 aft (see FIG. 6A); closing the linkage 52 moves the slider forward (see FIG. 6B).

Figure 7A:
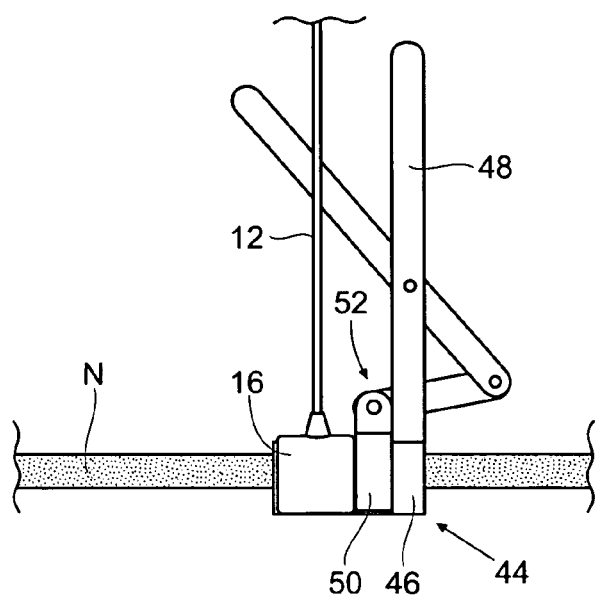
FIG. 7A is a side view of the applicator tool shown in FIG. 6C, with the electrode mounted and the electrode delivery mechanism in an aft condition, ready to implant the electrode about a nerve.

The inverted trough shape of the applicator body 46 is sized and configured so that, when the slider 50 is in is aft position, the electrode 12 can be uncoiled and mounted on the body 46 forward of the slider 50, as FIG. 6C shows. This is desirably accomplished immediately before placing the applicator tool 44 in the targeted position on the nerve N, which is shown in FIG. 7A.

Figure 7B:
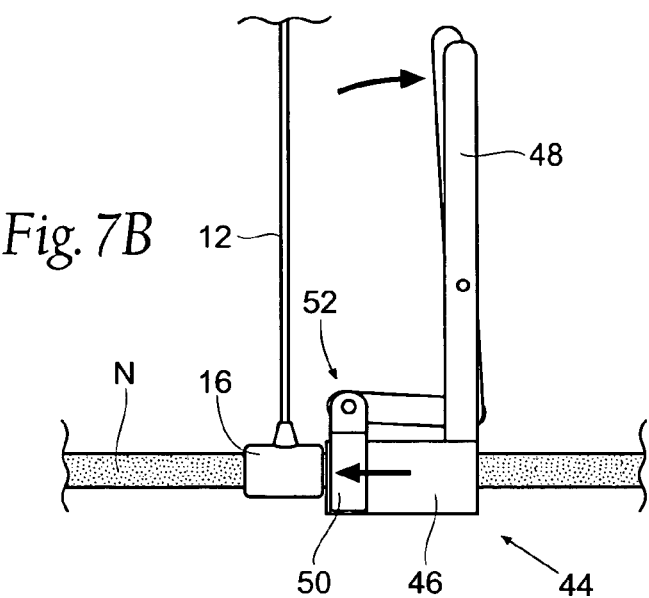
FIG. 7B is a side view of the applicator tool shown in FIG. 7A, with the electrode delivery mechanism translated to a forward condition to implant the electrode about a nerve.
Figure 7C:
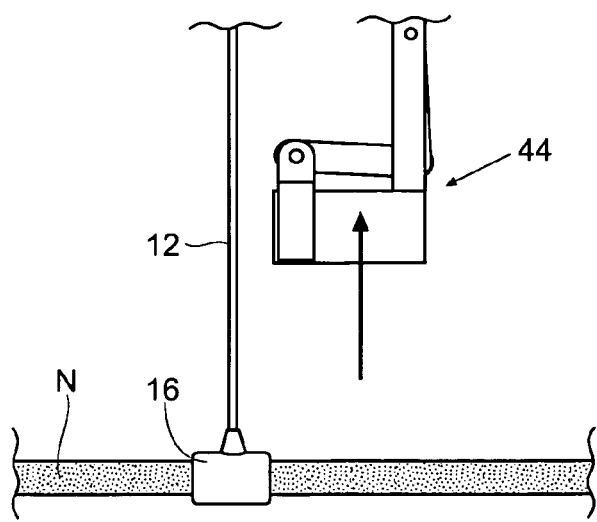
FIG. 7C is a side view of the applicator tool shown in FIG. 7A, after implantation of the electrode about a nerve and withdrawal of the application tool from the nerve.

Closing the linkage 52 (as FIG. 7B shows), moves the slider 50 forward. The slider pushes against the electrode 16 and ultimately ejects the electrode 16 from the applicator body 46 onto the nerve N (as FIG. 7B shows). Free of the trough-shaped applicator body 46, the elastic memory of the molded electrode 16 causes it to coil about the nerve N, as FIGS. 1 and 3A show. The applicator tool 44 can now be removed from the nerve N, leaving the electrode 16 implanted about it (as FIG. 7C shows).

The applicator tool 44 can be formed of a metal or plastic material. Desirably, the tool 44 is molded from snap together medical grade plastic parts (e.g., polystyrene), and is supplied as part of a sterile kit with the electrode 16 as a single-use device.

The applicator tool 44 makes possible a straightforward and reliable placement of the electrode 16 into humans and animals, e.g., installation in vivo desirably is accomplished in one minute or less.

IV. Representative Indications

There are various conditions and diseases where use of the molded cuff electrode 16 to apply high frequency nerve block therapy may be indicated.

A. Cerebral Palsy

Cerebral Palsy (CP) is a condition that includes a broad category of symptoms that involve impairment of motor control due to central nervous system (CNS) injury occurring around the time of birth.

There is no standard therapy that works for all patients or all symptoms. Drugs can be used to control seizures and muscle spasms, and special braces can compensate for muscle imbalance. Surgery and mechanical aids may help to overcome some impairments; counseling for emotional and psychological needs, and physical, occupational, speech, and behavioral therapy may also be employed.

One dominant symptom of CP is spasticity of muscles. If the spasticity is not controlled, then contractures develop. Once this happens, the muscles are permanently shortened and function is compromised. By implanting bilateral two channel high frequency nerve blocks, one on each obdurator nerve and the other on each tibial nerve, action potential conduction to the gluteals and the adductors can be blocked at night. The nerve block can be turned off during the day and the patient can still have volitional control over the muscles.

A more advanced application of this technology would be to monitor EMG signals on the nerve or muscle and automatically detect the start of a spasm. Once detected, the nerve block would be applied to the related muscles to prevent the spasm.

One of the most effective treatments today for spasticity in CP patients is the Baclofen pump. This provides general systemic relief to the CP patient. However, it needs to be refilled every two to four months and has to be carefully set up. Also, the fact that it is systemic means that it may have unwanted side effects.

The United Cerebral Palsy Society estimates incidence in the US in 2002 to be 9500; prevalence is 550,000. They did note that incidence has been dropping due to better neo and post natal care. Since CP patients are typically identified as children, the parents (and others) have to consider a lifetime of care options.

B. Other CNS Conditions

Other conditions that result in spasticity are Multiple Sclerosis (MS), Stroke, Spinal Cord injury and other CNS conditions. Stroke, with a high incidence and prevalence (750,000/yr and 5 million), is a possible target application but stroke patients, with a much older average age, may not be as likely to consider surgery as a treatment alternative. However, MS patients are younger and more active and might be a suitable target population. A 2002 study estimated that approximately 200,000 to 350,000 Americans suffer from MS, with an incidence of 10,000 people per year. Older studies suggest that it affects about 1.1 million people worldwide. The incidence appears to be increasing in women.

C. Phantom Pain in Amputations

Neuromas (and phantom pain in amputations) are an enlargement of the sheath of the nerve. Neuromas sometimes develop after amputation of a limb. They are frequently intractable and very painful.

It is estimated that there are 350,000 amputees living in the United States, with approximately 135,000 new amputations occurring each year. The number of amputees worldwide is not currently tracked by any organization. In the United States, the most common causes of amputation of the lower extremity are disease (70%), trauma (22%) congenital or birth defects (4%) and tumors (4%). Upper extremity amputation is usually due to trauma or birth defect with disease not as great of a contributing factor.

In one form or another pain is experienced by virtually 100% of people following an amputation. Immediate post-op pain is the pain experienced after any surgical procedure where skin, muscle, bone and nerves are cut. Essentially everyone experiences some degree of post-op pain following an amputation. It can usually be controlled with pain medication and subsides fairly rapidly as swelling goes down, tissues begin to heal, and the wound stabilizes.

But long term pain in the residual limb significantly affects as many as 40% of the amputees more than a year after amputation. Neuromas are only one of the underlying causes of post-amputation pain.

The use of the high frequency nerve block would address the some of the intractable chronic pain following an amputation by blocking the action potentials in the afferent nerves.

D. Trigeminal Neuralgia

Trigeminal Neuralgia causes severe intractable episodes of facial pain that are poorly controlled by medication and often chronic in nature. Last resort treatment often includes transection of the trigeminal nerve which relieves the pain but also causes paralysis of some of the muscles in the face.

The use of the high frequency nerve block would address the same type of the intractable chronic pain following an amputation by blocking the action potentials in the afferent nerves. A reversible nerve block offers a superior solution by blocking the pain as needed and reversing the block when not needed.

We claim:

1. A system for placement of an implantable cuff electrode about a biological tissue, the system comprising:
    an elastic body comprising a single layer of elastomeric material, the elastic body having an elastic memory to form a normally coiled configuration extending as a spiral having an inner diameter and a range of about 450 degrees to about 560 degrees, the elastic body being configured to be elastically uncoiled to increase the inner diameter in response to an uncoiling force,
    at least one electrically conductive surface coupled to an inside surface of the elastic body,
    an applicator body having a handle, the applicator body comprising an open ended inverted trough for fitment over a portion of the biological tissue, the inverted trough sized and configured to apply the uncoiling force to the elastic body and maintain the elastic body and electrically conductive surface in an uncoiled configuration for placement about the biological tissue, the applicator body including a slider carried on the applicator body and moveable along the axis of the applicator body between a forward position and an aft position, the slider being capable of axially sliding the elastic body off the open ended inverted trough and onto the biological tissue, a linkage mechanism coupled to the handle and the slider to affect axial movement of the slider fore and aft, and the elastic body and electrically conductive surface being capable of assuming the normally coiled configuration after placement onto the biological tissue allowing intimate contact between the electrically conductive surface on the inside surface of the elastic body and the biological tissue surrounded.

2. The system of claim 1:
wherein the at least one electrically conductive surface measures at least one mm of length along the axis of the biological tissue and at least one mm of width along the circumference of the biological tissue.

3. The system of claim 1:
wherein the elastic memory of the cuff electrode is capable of exerting a maximum pressure about a nerve of about 20 mm Hg.

4. The system of claim 1:
wherein the at least one electrically conductive surface is capable of making circumferential contact substantially about the entire periphery of the biological tissue.

5. The system of claim 1:
wherein the at least one electrically conductive surface is capable of making contact substantially along only a length of the biological tissue and around only a portion of the circumference of the biological tissue.

6. The system of claim 1:
wherein the elastic memory of the cuff electrode is adaptive to post-operative swelling by allowing the coiled configuration to expand and contract about a periphery of the biological tissue.

7. The system of claim 1:
wherein the elastic body and electrically conductive surface are capable of assuming the normally coiled configuration after placement onto at least one nerve.

8. The system of claim 1:
wherein the electrically conductive surface is segmented into isolated segments along the axis of the biological tissue or around the circumference of the biological tissue.

9. The system of claim 1:
wherein the electrically conductive surface comprises a thin film of metal deposited on a liquid crystal polymer substrate.

10. The system of claim 1:
wherein the cuff electrode includes three electrically conductive surfaces.

11. The system of claim 10:
wherein the three electrically conductive surfaces are individually electrically controllable.

12. The system of claim 1:
wherein the elastic body further includes a strain relief boot.

13. A system for neuronal recording and/or stimulating and/or blocking, the system comprising:
an implantable lead comprising an encapsulated wire element having a proximal end and a distal end, a stimulation pulse generator coupled to the proximal end of the wire element, a cuff electrode coupled to the distal end of the wire element, the cuff electrode comprising an elastic body comprising a single layer of elastomeric material, the elastic body having an elastic memory, and at least one electrically conductive surface coupled to the wire element and an inside surface of the elastic body, the elastic body having an elastic memory to form a normally coiled configuration extending as a spiral having an inner diameter and a range of about 450 degrees to about 560 degrees, the elastic body being configured to be elastically uncoiled to increase the inner diameter in response to an uncoiling force, an applicator body having a handle, the applicator body comprising an open ended inverted trough for fitment over a portion of the biological tissue, the inverted trough sized and configured to apply the uncoiling force to the elastic body and maintain the elastic body and electrically conductive surface in an uncoiled configuration for placement about the biological tissue, the applicator body including a slider carried on the applicator body and moveable along the axis of the applicator body between a forward position and an aft position, the slider being capable of axially sliding the elastic body off the open ended inverted trough and onto the biological tissue, a linkage mechanism coupled to the handle and the slider to affect axial movement of the slider fore and aft, the elastic body and electrically conductive surface being capable of assuming the normally coiled configuration after placement onto the biological tissue allowing intimate contact between the electrically conductive surface on the inside surface of the elastic body and the biological tissue surrounded, and wherein the proximal end of the lead is coupled to a stimulation pulse generator.

14. The system according to claim 13:
wherein the stimulation pulse generator generates electrical waveforms capable of depolarizing a nerve across its entire cross section or selectively over just a portion of the nerve cross section.

15. The system according to claim 13:
wherein the stimulation pulse generator generates a high frequency electrical waveform at a range of about 5 kHz to about 30 kHz.

16. The system according to claim 13:
wherein the elastic body further includes a strain relief boot.

* * * * *

UNITED STATES PATENT AND TRADEMARK OFFICE
CERTIFICATE OF CORRECTION

PATENT NO.         : 7,797,058 B2                                                                 Page 1 of 1
APPLICATION NO.    : 11/196995
DATED              : September 14, 2010
INVENTOR(S)        : Mrva et al.

It is certified that error appears in the above-identified patent and that said Letters Patent is hereby corrected as shown below:

Column 1, Line 2 of the paragraph under "Statement Regarding Federally Sponsored Research", after "grant no." delete "1RNS051862-01" and insert -- 1R43NS051862-01 --.

Column 1, Line 4 of the paragraph under "Statement Regarding Federally Sponsored Research", after "The Government" delete "may have" and insert -- has --.

Signed and Sealed this
Nineteenth Day of April, 2011

David J. Kappos
*Director of the United States Patent and Trademark Office*